United States Patent [19]

Lang et al.

[11] Patent Number: 5,261,926
[45] Date of Patent: Nov. 16, 1993

[54] PROCESS FOR DYEING KERATINOUS FIBERS COMBINING ISATIN OR ITS DERIVATIVES WITH A TRI-, TETRA- OR PENTASUBSTITUTED ANILINE OR WITH A BISPHENYLALKYLENEDIAMINE, AND DYEING AGENTS

[75] Inventors: Gerard Lang, Saint-Gratien; Jean Cotteret, Verneuil-sur-Seine, both of France

[73] Assignee: L'Oreal, Paris, France

[21] Appl. No.: 845,586

[22] Filed: Mar. 4, 1992

[30] Foreign Application Priority Data

Mar. 5, 1991 [FR] France ............... 91 02615

[51] Int. Cl.$^5$ ............................................... A61K 7/13
[52] U.S. Cl. ........................................ 8/406; 8/405; 8/408; 8/409
[58] Field of Search .......... 8/405, 406, 408, 409, 8/429; 548/485

[56] References Cited

U.S. PATENT DOCUMENTS

| | | | |
|---|---|---|---|
| 4,566,875 | 1/1986 | Grollier et al. | 8/409 |
| 4,750,908 | 6/1988 | Rosenbaum et al. | 8/405 |
| 4,921,503 | 5/1990 | Anderson et al. | 8/406 |
| 5,137,538 | 8/1992 | Madrange et al. | 8/421 |

FOREIGN PATENT DOCUMENTS 2626771  8/1989  European Pat. Off.
0359465  3/1990  European Pat. Off.

OTHER PUBLICATIONS

French Search Report of FR 91 02915.

Primary Examiner—Paul Lieberman
Assistant Examiner—William S. Parks
Attorney, Agent, or Firm—Cushman, Darby & Cushman

[57] ABSTRACT

The invention relates to a process for dyeing keratinous fibres, comprising the simultaneous or sequential application of a component (A) containing at least one compound of formula (I):

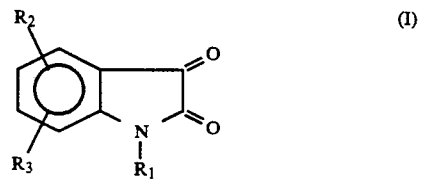

in which:

$R_1$ denotes hydrogen, alkyl, acetyl, benzoyl, phenyl or $C_1$-$C_4$ carboxyalkyl, $R_2$ and $R_3$ denote hydrogen, alkyl, alkoxy, hydroxyalkyl, amino, halogen, nitro, alkylphenyl, phenyl, alkylamino or hydroxyalkylamino, and a component (B) containing at least (i) a compound of formula (II):

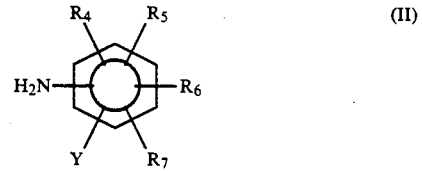

in which:

Y denotes OH or $NR_8R_9$, $R_8$ and $R_9$, which are identical or different, denote hydrogen, aminoethyl, hydroxyethyl or $C_1$-$C_4$ alkyl, $R_4$ to $R_7$ independently of each other denote a hydrogen atom, a $C_1$-$C_4$ alkyl, a chlorine, a $C_1$-$C_4$ alkoxy, an acetylamino, an aryloxy, not more than two of the groups $R_4$ to $R_7$ denote a hydrogen atom, excluding 2,5-dimethoxy-1,4-diaminobenzene, and the cosmetically acceptable salts, or (ii) a bisphenylalkylenediamine.

It also relates to the dyeing agents for implementing it.

16 Claims, No Drawings

PROCESS FOR DYEING KERATINOUS FIBERS COMBINING ISATIN OR ITS DERIVATIVES WITH A TRI-, TETRA- OR PENTASUBSTITUTED ANILINE OR WITH A BISPHENYLALKYLENEDIAMINE, AND DYEING AGENTS

The present invention relates to a process for dyeing keratinous fibers, in particular human hair, combining isatin or one of its derivatives with an aromatic diamine or a di-, tri- or tetrasubstituted aminophenol or with a bisphenylalkylenediamine, and to the dyeing agents used.

In direct dyeing of hair, that is to say in a dyeing process not utilising a process of development of dyes by an oxidative route, it has already been proposed to employ 2,3-indolinedione, also called isatin, as a basic yellow dye in French Patent No. 2,588,473.

European Application No. 0,359,465 later proposed a direct dyeing process employing isatin or one of its derivatives in combination with disubstituted aminobenzene derivatives.

The applicants have just found, surprisingly, a new dyeing process combining isatin or its derivatives with dyes of the tri- tetra- or pentasubstituted aniline type or with compounds of the bisphenylalkylenediamine type, enabling a wide range of shades to be obtained which are more resistant to shampooing and to perspiration than those obtained with the direct dyeing processes employing the known amino derivatives of the prior art. The colors obtained are additionally stable to light, to inclement weather and to chemical agents.

The subject of the present invention is therefore a process for dyeing keratinous fibers, consisting in applying to the fibers isatin or one of its derivatives and an aromatic diamine or a di-, tri- or tetrasubstituted aminophenol or a bisphenylalkylenediamine, either simultaneously in the form of an extemporaneous mixture, or successively.

Another subject of the invention also consists of a two-component dyeing agent.

Other subjects will appear in the light of the description.

The process for dyeing keratinous fibers, in particular human hair, in accordance with the present invention, is characterized essentially by the fact that it comprises the application to the said fibers of a component (A) consisting of a composition containing, in a suitable medium for dyeing, at least one compound of the following formula (I):

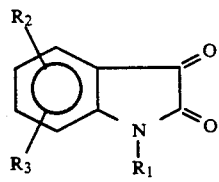

in which:
$R_1$ denotes a hydrogen atom or a $C_1$-$C_6$ alkyl, acetyl, benzoyl, phenyl or $C_1$-$C_4$ carboxyalkyl radical,
$R_2$ and $R_3$ independently of each other denote a hydrogen atom, a $C_1$-$C_6$ alkyl, a $C_1$-$C_4$ alkoxy, a hydroxyl, an amino, a halogen atom, a nitro group, an alkyl($C_1$-$C_6$)phenyl, phenyl, $C_1$-$C_6$ alkylamino, $C_1$-$C_6$ hydroxyalkylamino or poly($C_2$-$C_6$ hydroxyalkyl)amino, and a component (B) consisting of a composition containing, in a suitable medium for dyeing, at least
(i) an aromatic diamine or a di-, tri- or tetra-substituted aminophenol of the following formula (II):

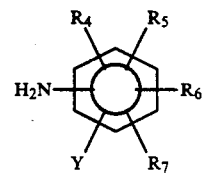

in which:
Y denotes OH or $NR_8R_9$,
$R_8$ and $R_9$, which are identical or different, denote hydrogen, aminoethyl, hydroxyethyl or $C_1$-$C_4$ alkyl,
$R_4$ to $R_7$ independently of each other denote a hydrogen atom, a $C_1$-$C_4$ alkyl, a chlorine, an acetylamino, a $C_1$-$C_4$ alkoxy or an aryloxy,
not more than two of the groups $R_4$ to $R_7$ denoting a hydrogen atom,
excluding 2,5-dimethoxy-1,4-diaminobenzene,
as well as the cosmetically acceptable salts of these compounds, or
(ii) a bisphenylalkylenediamine, called a double base, of formula (IV)

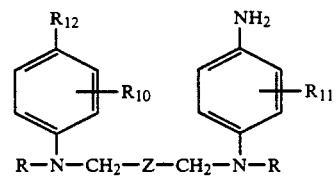

in which:
$R_{12}$ denotes a hydroxyl or $NHR_{13}$ group, where $R_{13}$ denotes a hydrogen atom or a lower alkyl radical,
$R_{10}$ and $R_{11}$, which are identical or different, denote either hydrogen atoms or halogen atoms or else alkyl groups,
R denotes a hydrogen atom or an alkyl, hydroxyalkyl or aminoalkyl group in which the amino residue may be substituted,
Z denotes a radical taken from the group consisting of the following radicals:

$$-(CH_2)_n-, \ -(CH_2)_{n'}-O-(CH_2)_{n'}-,$$

$$(CH_2)_{n'}-CHOH-(CH_2)_{n'}, \ -(CH_2)_{n'}-\underset{\underset{CH_3}{|}}{N}-(CH_2)_{n'}-,$$

n being an integer from 0 to 8 and n' an integer between 0 and 4, it being possible for this base to be in the form of its addition salts with acids.

Methyl, ethyl, n-propyl, n-butyl, isopropyl, isobutyl and tert-butyl radicals may be mentioned as $C_1$-$C_4$ alkyl radicals.

In addition to those mentioned above, the $C_1$-$C_6$ alkyl radicals include pentyl (linear and branched) and hexyl (linear and branched) radicals.

Methoxy, ethoxy, propoxy and butoxy radicals may be mentioned as $C_1-C_4$ alkoxy radicals.

Besides those mentioned above, the $C_1-C_6$ alkoxy radicals include pentyloxy and hexyloxy radicals.

Hydroxyethyl and 2- or 3-hydroxypropyl radicals may be mentioned as hydroxyalkyl radicals.

2,3-Dihydroxypropyl and 3,4-dihydroxybutyl may be mentioned as polyhydroxyalkyl radicals.

As for aryloxy radicals, phenyloxy and benzyloxy may be mentioned.

The cosmetically acceptable salts are chosen from hydrochlorides, hydrobromides and sulphates.

In the definition of the so-called double bases the alkyl or alkoxy radicals preferably denote a group containing 1 to 4 carbon atoms and especially methyl, ethyl, propyl, methoxy or ethoxy.

The process according to the invention may be used without involving any oxidizing agent other than air.

The dyeing process described above results in the formation of a Schiff base either during the mixing of the composition (A) with the composition (B) or in situ in the keratinous fiber during a sequential application of the compositions (A) and (B). This Schiff base has the formula:

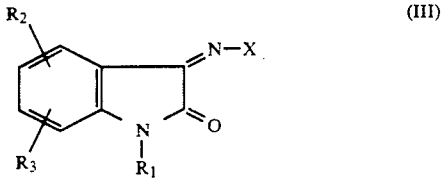

(III)

in which X denotes:

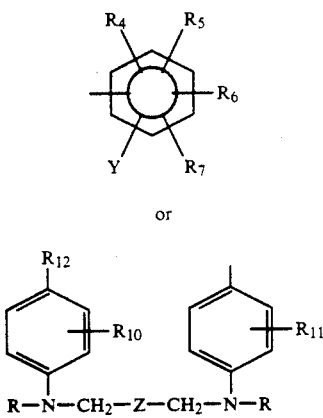

and Z, R, $R_{10}$ to $R_{12}$, Y and $R_4$ to $R_7$ having the meanings defined above.

Of the compounds of formula (I), isatin may be mentioned more particularly.

The preferred compounds of formula (II) are chosen from:
2-methoxy-3,5-dimethyl-1,4-diaminobenzene
2,6-dimethyl-4-bis(β-hydroxyethyl)amino-1-aminobenzene
5,6-dimethoxy-1,3-diaminobenzene
2,6-dimethyl-1,3-diaminobenzene
2,6-dimethoxy-1,3-diaminobenzene
2,6-dimethoxy-5-chloro-1,3-diaminobenzene
2,6-dimethoxy-3-β-hydroxyethylamino-1-aminobenzene
2,4-dimethoxy-3-β-hydroxyethylamino-1-aminobenzene
4,6-dibenzyloxy-1,3-diaminobenzene
3-methyl-6-methoxy-1,2-diaminobenzene
3,5-dimethyl-4-aminophenol
2,5-dimethyl-4-aminophenol
2,3,5-trimethyl-4-aminophenol
2,3,5,6-tetramethyl-4-aminophenol
4-chloro-5-acetylamino-2-aminophenol, and
4,6-diphenyloxy-1,3-diaminobenzene.

In addition to these preferred compounds the compounds of formula (II) which are more particularly preferred are chosen from:
2,6-dimethyl-1,4-diaminobenzene
2,5-dimethyl-1,4-diaminobenzene
2,3-dimethyl-1,4-diaminobenzene
2-methoxy-5-methyl-1,4-diaminobenzene
2-methoxy-5-methyl-4-β-aminoethylamino-1-aminobenzene
2-methyl-5-chloro-4-β-aminoethylamino-1-aminobenzene
4,6-dimethoxy-1,3-diaminobenzene
2,3-dimethyl-4-aminophenol
2,6-dimethyl-4-aminophenol, and
2,5-dimethyl-3-aminophenol.

Of the compounds of formula (IV) there may be mentioned N,N'-bis(β-hydroxyethyl)-N,N'-bis(4'-aminophenyl)-1,3-diamino-2-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine and N,N'-bis(ethyl)-N,N'-bis(4'-amino-3'-methylphenyl)ethylenediamine.

According to the process of the present invention the compounds of formula (I) are preferably present in the component (A) in proportions of between 0.01 and 5% by weight and more particularly between 0.25 and 2% by weight relative to the total weight of the component (A) or of the components (A)+(B) and the compounds of formula (II) or (IV) are present in the component (B) in proportions which are preferably between 0.01 and 5% by weight and in particular between 0.25 and 2% by weight relative to the total weight of the component (B) or of the components (A)+(B).

The components (A) and (B) which may be employed in accordance with the invention are liquid, more or less thickened, aqueous or anhydrous compositions, creams, aqueous or anhydrous gels, oils or powders to be diluted with a liquid at the time of use, also called poultices.

In a first form of embodiment of the invention the suitable cosmetic medium for dyeing is aqueous and has a pH which can vary between 2 and 10 and preferably between 3 and 9.5; it is adjusted to the desired value with the aid of alkalifying agents or acidifying agents which are known per se.

These compositions may contain anionic, cationic, nonionic or amphoteric surface-active agents or mixtures thereof. These surfactants are present in the compositions in accordance with the invention in proportions of between 0.1 and 55% by weight, and preferably between 1 and 40% by weight relative to the total weight of each composition.

These aqueous compositions may contain organic solvents, among which there may be mentioned by way of example lower alkanols such as ethanol or isopropanol, polyols such as glycerol, glycols or glycol ethers such as ethylene glycol, propylene glycol, ethylene glycol monobutyl ether, diethylene glycol monoethyl ether and monomethyl ether and similar products or mixtures thereof.

These solvents are preferably employed in proportions ranging from 1 to 60% by weight and more particularly from 3 to 30% by weight relative to the total weight of each composition.

These compositions may be thickened with agents chosen from sodium alginate, gum arabic, guar or carob gum, xanthan gum, scleroglucans, pectins, cellulose derivatives and various polymers which have a thickening action such as acrylic acid derivatives. Inorganic thickening agents such as bentonite may also be employed.

These thickening agents are preferably present in proportions between 0.1 and 5% by weight and in particular between 0.5 and 3% by weight relative to the total weight of each composition.

These compositions may also contain anionic, nonionic, cationic or amphoteric monomers or mixtures thereof, in proportions of 0.1 to 5% by weight relative to the total weight of each composition.

These compositions may, of course, contain any other adjuvants usually employed in compositions for hair dyeing, such as penetrating agents, sequestering agents, antioxidants, buffers, perfumes, dyes and the like.

A preferred form of the invention consists in employing an anhydrous medium as described in French Patent No. 2,526,031.

An anhydrous medium means a medium containing not more than 1% of water.

The anhydrous medium consists, in accordance with this alternative form of the invention, of a mixture of at least one anhydrous solvent and of one or more anhydrous surface-active agents, so that these compositions contain at least 15% of solvent and at least 20% of surface-active agent.

The solvents employed are cosmetically acceptable solvents chosen from saturated $C_2$-$C_{20}$ monoalcohols such as ethanol, isopropanol, cetyl alcohol or octyldodecanol, polyols such as alkylene glycols like ethylene glycol, propylene glycol, glycerol and diethylene glycol, glycol ethers such as mono-, di- and triethylene glycol monoalkyl ethers, such as, for example, ethylene glycol monoethyl ether, ethylene glycol monobutyl ether and diethylene glycol monoethyl ether, esters such as, for example, ethylene glycol monomethyl ether acetate and ethylene glycol monoethyl ether acetate, and esters of fatty acids and of saturated lower alcohols such as isopropyl myristate or palmitate.

Particularly preferred compositions contain a solvent chosen from ethanol, cetyl alcohol, propylene glycol, ethylene glycol monoethyl ether or ethylene glycol monobutyl ether.

The surface-active agents employed in this form of embodiment are chosen from anhydrous surface-active agents of anionic, nonionic, cationic or amphoteric type or mixtures thereof. There may be mentioned more particularly polyoxyethylenated fatty alcohols, polyoxyethylenated alkylphenols or naphthols, monoalkyltrimethylammonium halides, dialkyldimethylammonium halides, soaps and polyglycerolated fatty alcohols. The preferred surface-active agents are nonionic surface-active agents.

These compositions may contain an anhydrous alkaline or acidifying agent such as, for example, citric acid, ascorbic acid, acetic acid, lactic acid and alkanolamines such as, preferably, those which are completely substituted on the amine group, like dimethylaminoethanol.

Apart from the compounds described above, the anhydrous compositions in accordance with the invention may contain numerous additives which can be employed in cosmetics, the only condition being that they should contain less than 1% of water. Among these additives there may be mentioned perfumes, thickening agents, treating agents antioxidants, vegetable or mineral oils, preserving agents and organic salts.

These compositions may be applied as such to wet hair or may be diluted just before use. In the latter case, at the time of dyeing, the compositions according to the invention are diluted with an aqueous solution so that the ratio of the composition according to the invention to the aqueous solution is between 0.25 and 2. The aqueous solution may consist of pure water, but also of any other complex aqueous liquid which is more or less thickened such as, for example, a carrier usually employed in hair dyeing compositions.

In this case, the components of the cosmetic medium may be all kinds of cosmetically acceptable ingredients, anhydrous or otherwise, which are usually employed in a composition of this type and described generally above.

Another form of use of the components (A) and/or (B) in accordance with the invention consists of the use in the form of poultices, that is to say in the form of powder to be diluted with a liquid at the time of use.

In this form of embodiment the dyes are prepared in the form of a powder which is stable in storage and are introduced into a solid medium which may consist of powders, flours or starchy or mucilaginous substances which are diluted at the time of use with a suitable liquid so as to form a mixture of a consistency which is appropriate for being applied to the head.

The powders or flours employed in a composition of this type generally consist of insoluble substances such as silicas, clays or plants which have been pulverized after their active principles have been extracted with solvent.

The liquid may consist of water or of mixtures of water and of cosmetically acceptable solvents such as alcohols or glycols or of oils.

The liquid medium is added to the powder in proportions such as that after mixing a paste is obtained which has a viscosity of between 0.3 and 5 Pa s.

A subject of the invention consists of a dyeing agent for keratinous fibers, in particular human hair, characterized in that it consists of the components (A) and (B) which are stored in separate form and are as defined above.

The components (A) and (B) are intended either to be mixed just before use or to be applied successively to the fibers to be treated.

According to one form of embodiment the different components (A) and (B) may be packaged in a multicompartment device also called a dyeing kit, comprising all the components intended to be applied in the case of the same single dyeing operation to keratinous fibers, in particular hair, in successive applications with or without premixing.

Such devices may comprise a first compartment containing the component (A) including isatin or its derivatives of formula (I) and a second compartment containing the component (B) including tri-, tetra- or pentasubstituted aniline of formula (II) or the bisphenylalkylenediamine of formula (IV).

Another alternative form may also consist in storing the component (A) or the component (B) in an anhydrous solvent medium and in providing a third compartment containing an aqueous medium which is suitable for dyeing and cosmetically acceptable. In this case, the content of the third compartment is mixed just before use in either or both of the two compartments containing the anhydrous components (A) and (B) or else the three compartments are mixed before use.

According to an alternative form the process of the invention consists in mixing the component (A) with the component (B) just before use, the resulting composition being applied to the hair for 5 to 40 minutes and preferably 20 to 30 minutes. The hair is then rinsed, The following examples are intended to illustrate the invention without, however, being limiting in nature.

EXAMPLES 1 to 15

Hair dyeing is undertaken by applying 20 g of the compositions to naturally grey hair containing 90% of white.

The compositions are prepared just before use.

The composition is left to act for 20 minutes and the hair is then rinsed, shampooed and then rinsed again. After drying, the hair is dyed the shade specified at the bottom of Table I below.

TABLE I

| in g AS | 1 | 2 | 3 | 4 | 5 | 6 | 7 | 8 | 9 | 10 |
|---|---|---|---|---|---|---|---|---|---|---|
| Isatin | 1 | 1 | 1 | 1 | 1 | 1 | 1 | 1 | 1 | 1 |
| 2-Methoxy-4-β-aminoethyl-amino-5-methyl-1-amino-benzene, 3HCl | 1 | | | | | | | | | |
| 2-Methyl-4-β-aminoethyl-amino-5-chloro-1-amino-benzene, 3HCl | | 1 | | | | | | | | |
| 4,6-Dimethoxy-1,3-diamino-benzene, 2HCl | | | 1 | | | | | | | |
| 2,3-Dimethyl-para-aminophenol | | | | 1 | | | | | | |
| 2,6-dimethyl-para-aminophenol | | | | | 1 | | | | | |
| 2,5-dimethyl-meta-aminophenol | | | | | | 1 | | | | |
| 2,3,5,6-Tetramethyl-para-aminophenol | | | | | | | 1 | | | |
| 4-Chloro-5-acetylamino-ortho-aminophenol | | | | | | | | 1 | | |
| 2,5-Dimethyl-1,4-diamino-benzene | | | | | | | | | 1 | |
| 2,3-dimethyl-1,4-diamino-benzene | | | | | | | | | | 1 |
| Ethyl alcohol | 30 | 30 | 30 | 30 | 30 | 30 | 30 | 30 | 30 | 30 |
| Triethanolamine q.s. pH | 7.9 | 8 | 8 | | 8 | | 8 | 8 | 8 | 8 |
| Spontaneous pH | | | | 8.1 | | 8 | | | | |
| Water q.s. | 100 | 100 | 100 | 100 | 100 | 100 | 100 | 100 | 100 | 100 |
| Shades obtained | purple-violet | golden coppery | very light blond | coppery | coppery | matt golden | coppery golden | sl. ashen natural very light blond | coppery golden | coppery golden |

| in g AS | 11 | 12 | 13 | 14 | 15 |
|---|---|---|---|---|---|
| Isatin | 1 | | 1 | 1 | 0.5 |
| 6-Bromoisatin | | 1 | | | |
| 2,6-Dimethyl-1,4-diaminobenzene | 1 | 1 | | | |
| 2-Methoxy-5-methyl-1,4-diaminobenzene | | | 1 | | 0.5 |
| 2-Methoxy-3,5-dimethyl-1,4-diamino-benzene | | | | 1 | |
| Ethyl alcohol | 30 | 30 | 30 | 30 | 30 |
| Sodium lauryl ether sulphate oxyethylenated with 2 moles of ethylene oxide, containing 28% AS | | | | | 8.4 |
| Triethanolamine q.s. pH | 8 | 8 | 8 | 8 | 8 |
| Water q.s. | 100 | 100 | 100 | 100 | 100 |
| Shades obtained | sl. red coppery | pearly beige light blond | coppery mahogany | matt golden | coppery pearly blond | shampooed, rinsed again and then dried.

According to another alternative from the process of the invention consists in applying to the hair at least one component (A) and, before or after the component (A), the component (B), such as are defined above, in leaving each to act for 5 to 40 minutes, preferably 20 to 30 minutes, optionally rinsing with water between the two stages. The hair is then rinsed, shampooed, rinsed again and then dried.

EXAMPLE 16

The procedure is as in Example 14, with 2-methoxy-5-methyl-1,4-diaminobenzene replaced with N,N'-bis(β-hydroxyethyl)-N,N'-bis(4'-aminophenyl)-1,3-diamino-2-propanol, 3HCl.

After drying, the hair is dyed a coppery mahogany shade.

EXAMPLE 17

At the time of use the composition (A) is mixed with twice its weight of water and the composition (B) with 1.5 times its weight of water. 20 g of the composition (A) (pH 8.6) are applied to 3 g of natural grey hair containing 90% of white.

The composition is left to act for 15 minutes and, after rinsing, 20 g of the composition (B) (pH 9.2) are applied for 15 minutes, the hair is rinsed, shampooed and then rinsed again. After drying, the hair is dyed the shade specified at the bottom of Table II below.

TABLE II

| in g AS | 17 | |
|---|---|---|
| | Comp. A | Comp.B |
| Isatin | 4 | |
| 2,6-Dimethyl-1,4-diaminobenzene | | 1 |
| Carob gum sold under the name Vidogum L 175 by Sanofi Bio Industrie | 3 | |
| Calcium carbonate | 8 | |
| Spent soapwort residue powder of particle size below 90 microns | 35 | |
| Skimmed milk powder q.s. | 100 | |
| Ethyl alcohol | | 28.5 |
| N,N-Dimethylamino-2-ethanol | | 1 |
| Nonylphenol oxyethylenated with 9 moles of ethylene oxide q.s. | | 100 |
| Shade obtained | | light blond beige |

What is claimed is:

1. A process for dyeing keratinous fibers comprising applying to said fibers a component (A) comprising a composition containing, in a medium suitable for dyeing said fibers, at least one compound of formula (I):

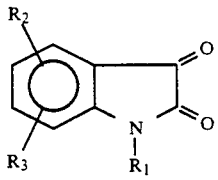

(I)

wherein $R_1$ represents hydrogen, $C_1$-$C_4$ alkyl, acetyl, benzoyl, phenyl or $C_1$-$C_4$ carboxyalkyl, $R_2$ and $R_3$, each independently, represent hydrogen, $C_1$-$C_6$ alkyl, $C_1$-$C_4$ alkoxy, hydroxyl, amino, halogen, nitro, alkyl ($C_1$-$C_6$) phenyl, $C_1$-$C_6$ alkylamino, $C_1$-$C_6$ hydroxyalkylamino or poly ($C_2$-$C_6$ hydroxyalkyl) amino, and a component (B) comprising a composition containing, in a medium suitable for dyeing said fibers, at least (i) an aromatic diamine or a di-, tri- or tetrasubstituted aminophenol of formula (II):

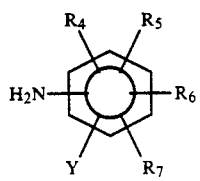

(II)

wherein

Y represents OH or $NR_8R_9$, $R_8$ and $R_9$, each independently, represent hydrogen, aminoethyl, hydroxyethyl or $C_1$-$C_4$ alkyl, $R_4$ to $R_7$, each independently, represent hydrogen, $C_1$-$C_4$ alkyl, chlorine, acetylamino, $C_1$-$C_4$ alkoxy or aryloxy, with the proviso that not more than two of $R_4$ to $R_7$ groups represent hydrogen and excluding 2,5-dimethoxy-1,4-diaminobenzene, and the cosmetically acceptable salts of the compound of formula (II), or (ii) a bisphenylalkylenediamine, called a double base having formula (IV)

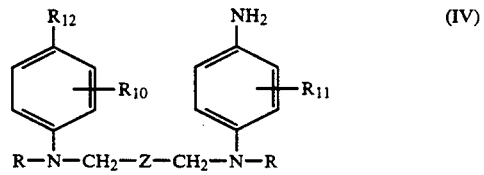

(IV)

wherein $R_{12}$ represents a hydroxyl or $NHR_{13}$ wherein $R_{13}$ represents hydrogen or lower alkyl, $R_{10}$ and $R_{11}$, each independently, represent hydrogen, halogen or alkyl, R represents hydrogen, alkyl, hydroxyalkyl or aminoalkyl wherein the amino moiety is optionally substituted, Z represents $-(CH_2)_n-$, $-(CH_2)_{n'}-O-(CH_2)_{n'}-$, $(CH_2)_{n'}-CHOH-(CH_2)_{n'}-$ or $-(CH_2)_{n'}$

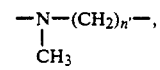

wherein n is an integer ranging from 0 to 8 and n' is an integer ranging from 0 and 4, and the acid addition salts thereof, the compound of formula (I) in said component (A) being present in an amount ranging from 0.01 to 5 percent by weight relative to the weight of said component (A) or to the total weight of components (A) and (B) and wherein the compounds of formula (II) or (IV) in said component (B) are present in an amount ranging from 0.01 to 5 percent by weight to the weight of said component (B) or to the total weight of components (A) and (B).

2. The process of claim 1 wherein said compound of formula (I) is isatin.

3. The process of claim 1 wherein the compound of formula (II) is selected from the group consisting of
2-methoxy-3,5-dimethyl-1,4-diaminobenzene,
2,6-dimethyl-4-bis(β-hydroxyethyl)amino-1-aminobenzene,
5,6-dimethoxy-1,3-diaminobenzene,
2,6-dimethyl-1,3-diaminobenzene,
2,6-dimethoxy-1,3-diaminobenzene,
2,6-dimethoxy-5-chloro-1,3-diaminobenzene,
2,6-dimethoxy-3-β-hydroxyethylamino-1-aminobenzene,
2,4-dimethoxy-3-β-hydroxyethylamino-1-aminobenzene,
4,6-dibenzyloxy-1,3-diaminobenzene,
3-methyl-6-methoxy-1,2-diaminobenzene,
3,5-dimethyl-4-aminophenol,
2,5-dimethyl-4-aminophenol,
2,3,5-trimethyl-4-aminophenol, 2,3,5,6-tetramethyl-4-aminophenol,
4-chloro-5-acetylamino-2-aminophenol, and
4,6-diphenyloxy-1,3-diaminobenzene.

4. The process of claim 1 wherein the compound of formula (II) is selected from the group consisting of
2,6-dimethyl-1,4-diaminobenzene,
2,5-dimethyl-1,4-diaminobenzene,
2,3-dimethyl-1,4-diaminobenzene,
2-methoxy-5-methyl-1,4-diaminobenzene,
2-methoxy-5-methyl-4-β-aminoethylamino-1-aminobenzene,
2-methyl-5-chloro-4-β-aminoethylamino-1-aminobenzene,
4,6-dimethoxy-1,3-diaminobenzene,
2,3-dimethyl-4-aminophenol,
2,6-dimethyl-4-aminophenol and
2,5-dimethyl-3-aminophenol.

5. The process of claim 1 wherein said bisphenylalkylenediamine of formula (IV) is selected from the group consisting of
N,N'-bis(β-hydroxyethyl)-N,N'-bis(4'-aminophenyl)-1,3-diamino-2-propanol,
N,N'-bis(β-hydroxyethyl)-N,N'-bis(4'-aminophenyl)ethylenediamine,
N,N'-bis(4-aminophenyl)tetramethylenediamine,
N,N'-bis(β-hydroxyethyl)-N,N'-bis(4-aminophenyl)tetramethylenediamine and
N,N'-bis(ethyl)-N,N'-bis(4'-amino-3'-methylphenyl)ethylenediamine.

6. The process of claim 1 wherein said component (A) or said compound (B) or both, is an aqueous or anhydrous composition in a thickened liquid form or a composition in the form of a cream, an aqueous or anhydrous gel, an oil or a powder to be diluted with a liquid at the time of use.

7. The process of claim 6 wherein said component (A) or said component (B), or both, is in the form of an aqueous composition having a pH ranging from 2 to 10, said aqueous composition also containing at least one cosmetically acceptable adjuvant selected from an anionic, cationic or nonionic surfactant, or a mixture thereof; an organic solvent; an anionic, nonionic, cationic or amphoteric polymer or a mixture thereof; a thickening agent; a penetrating agent; a sequestering agent; an antioxidant; a buffer; a dye; and a perfume.

8. The process of claim 6 wherein said component (A) or said compound (B), or both, is in the form of an anhydrous composition containing at least one anhydrous solvent present in an amount of at least 15 weight percent and at least one anhydrous surfactant present in an amount of at least 20 weight percent.

9. The process of claim 8 wherein said anhydrous solvent is selected from a saturated $C_2$–$C_{20}$ monoalcohol, a polyol, a glycol ether, a glycol ester and a fatty acid ester of a lower alcohol.

10. The process of claim 6 wherein said component (A) or said component (B), or both, is in the form of a powder to be diluted with a liquid at the time of use, said powder comprising a starchy or mucilaginous substance or a powder or flour selected from a silica, a clay or a plant pulverized after extraction of its active principles with a solvent.

11. The process of claim 10 which includes adding a cosmetically acceptable liquid to said component (A) or said component (B), or both, in powder form, in an amount sufficient so as to produce a poultice having a viscosity of 0.3 to 5 Pa s.

12. The process of claim 1 wherein said components (A) and (B) are mixed just before application to said fibers and the resulting composition is immediately applied to said fibers and wherein said composition is permitted to remain in contact with said fibers for a period of time ranging from 5 to 40 minutes, after which said fibers are rinsed, shampooed, rinsed again and dried.

13. The process of claim 1 wherein the application of said component (A) to said fibers is preceded by or followed by the application of said component (B) to said fibers, said fibers optionally being rinsed with water intermediate the application of said components to said fibers, and each of said component (A) and component (B) being permitted to remain in contact with said fibers for a period of time ranging from 5 to 40 minutes, after which said fibers are rinsed, shampooed, rinsed again and dried.

14. A dyeing agent for keratinous fibers comprising components (A) and (B) as defined in claim 1, in separate form, to be admixed together just before use or to be successively applied to said fibers to be treated.

15. A multi-compartment device or dyeing kit comprising at least two compartments, a first of which contains a component (A) as defined in claim 1 and a second of which contains a component (B) as defined in claim 1.

16. The device of claim 15 wherein said component (A) or said component (B), or both, is in the form of an anhydrous composition and said device includes a third compartment containing a cosmetically acceptable aqueous medium suitable for dyeing keratinous fibers and intended to be mixed before use with one or both of the contents of said first and second compartments.

* * * * *